US00PP29000P3

(12) United States Plant Patent
Velazquez

(10) Patent No.: US PP29,000 P3
(45) Date of Patent: Feb. 27, 2018

(54) ***DAPHNE* PLANT NAMED 'MONMKIE'**

(50) Latin Name: *Daphne burkwoodii*
Varietal Denomination: MonMkie

(71) Applicant: Cesar Velazquez, Salem, OR (US)

(72) Inventor: Cesar Velazquez, Salem, OR (US)

(73) Assignee: Monrovia Nursery Co., Azusa, CA (US)

( * ) Notice: Subject to any disclaimer, the term of this patent is extended or adjusted under 35 U.S.C. 154(b) by 136 days.

(21) Appl. No.: 14/757,331

(22) Filed: Dec. 16, 2015

(65) Prior Publication Data

US 2017/0181346 P1 Jun. 22, 2017

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Daphne* cultivar named 'MonMkie' is disclosed, characterized by variegated leaves with a wide, light yellow to yellow-white margin. Foliage is distinctively oblanceolate and broader than typical for species. The new cultivar is a *Daphne*, suitable for ornamental garden purposes.

1 Drawing Sheet

Latin name of the genus and species: *Daphne burkwoodii.*
Variety denomination: 'MONMKIE'.

BACKGROUND OF THE INVENTION

The new cultivar is a product of a chance discovery in a commercial setting by the inventor. In 2006, the inventor, Cesar Velazquez discovered an interesting single branch mutation in a commercial planting of the unpatented parent variety *Daphne burkwoodii* 'Carol Mackie'. This single branch mutation was discovered at a commercial nursery in Dayton, Oreg.

During 2006 the inventor propagated the interesting mutation by semi-hardwood cuttings at the commercial nursery in Dayton, Oreg. The initial propagation showed the mutation to be stable and additional generations were propagated, also by semi-hardwood cuttings. Approximately 5 generations have been reproduced since 2006, and have shown that the unique features of this cultivar are stable and reproduced true to type.

SUMMARY OF THE INVENTION

The cultivar 'MonMkie' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonMkie' These characteristics in combination distinguish 'MonMkie' as a new and distinct *Daphne* cultivar:

1. Variegated leaves with a wide, light yellow to yellow-white margin.
2. Variegation begins yellow, turning yellow-white with maturity.
3. Abundant small flowers.

4. Foliage oblanceolate and broader than typical for species.

COMPARISON TO PARENT VARIETY

Plants of the new cultivar 'MonMkie' are similar to plants of the parent; *Daphne burkwoodii* 'Carol Mackie' in most horticultural characteristics, however, plants of the new cultivar 'MonMkie' differ in the following:

1. Plants of the new variety produce foliage with a significantly wider, light yellow to yellow-white margin.
2. Plants of the new variety produce wider foliage than the parent variety.

COMMERCIAL COMPARISON

'MonMkie' can be compared to the commercial variety *Daphne burkwoodii* 'Somerset', unpatented. Plants of the new cultivar 'MonMkie' are similar to plants of 'Somerset' in most horticultural characteristics, however, plants of the new cultivar 'MonMkie' differ in the following:

1. Plants of the new variety produce foliage with a wide light yellow to yellow-white margin. Plants of this comparator produce solid green foliage.
2. Plants of the new variety produce wider foliage than this comparator variety.
3. Plants of the new variety are denser and bushier than plants of this comparator.

'MonMkie' can be compared to the commercial variety *Daphne burkwoodii* 'Brigg's Moonlight', unpatented. Plants of the new cultivar 'MonMkie' are similar to plants of 'Brigg's Moonlight' in most horticultural characteristics, however, plants of the new cultivar 'MonMkie' differ in the following:

1. Plants of the new variety produce foliage with a wide light yellow to yellow-white margin. Plants of this comparator produce light yellow foliage with a green margin.

2. Plants of the new variety produce wider foliage than this comparator variety.
3. Plants of the new variety are much denser and bushier than plants of this comparator.
4. Plants of the new variety are more tolerant of poor soil conditions than plants of this comparator.

BRIEF DESCRIPTION OF THE PHOTOGRAPH

The accompanying photograph in FIG. 1 illustrates in full color a typical young plant of 'MonMkie' grown outdoors in Oregon. The plant is approximately 6 months old, and is planted in a 3 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonMkie' plants grown outdoors in Dayton, Oreg. Plants are approximately 2 years old, in a 3 gallon nursery container. Temperatures ranged from −8° C. to 20° C. at night to 5° C. to 35° C. during the day. Measurements and numerical values represent averages of typical plant types. Botanical classification: *Daphne burkwoodii* 'MonMkie'.

PROPAGATION

Time to rooting: Approximately 4 to 8 weeks at approximately 20° C. to 30° C. from semi-hardwood cuttings.
Root description: Fine, fibrous young roots. Older roots becoming woody.

PLANT

Growth habit: Upright and outwardly spreading shrub. Moderately dense. Semi-evergreen.
Height: Approximately 55 cm.
Plant spread: Approximately 70 cm.
Branching characteristics: Above average branching for a *Daphne*, average 5 to 6 main branches, angled approximately 45 to 70 degrees on average.
Length of lateral branches: Approximately 15 cm.
Diameter of lateral branches: Average range 0.8 cm to 1.2 cm.
Lateral branch strength: Very strong, with some flexibility.
Lateral branch color: Young branches near RHS Yellow-Green 144A, flushed Greyed-Purple 187A. Mature branches: Near RHS Grey-Brown 199B heavily flushed Greyed-Purple N186A.
Other stem or plant characteristics: No pubescence or lenticels observed. Texture moderately rough and striated.
Number of leaves per lateral branch: Average 14 to 18.
Age of plant described: Approximately 2 years.

FOLIAGE

Leaf:
- *Type*.—Simple.
- *Arrangement*.—Alternate.
- *Average length*.—Approximately 8.5 to 9.5 cm.
- *Average width*.—Approximately 2.5 cm.
- *Shape of blade*.—Oblanceolate.
- *Apex*.—Mucronate when young, becoming acute with maturity.
- *Base*.—Attenuate.
- *Attachment*.—Sessile.
- *Margin*.—Entire.
- *Aspect*.—Undulating to slightly twisted.
- *Texture of top surface*.—Smooth.
- *Texture of bottom surface*.—Smooth.
- *Leaf internode length*.—Approximately 0.6 to 1.5 cm.
- *Color*.—Young foliage upper side: Center near RHS Green 137A. Margin near Yellow 8D. Margin width ranges from approximately 0.5 cm to 1.0 cm wide. Young foliage under side: Center near RHS Green 137A. Margin near Yellow 8D. Margin width ranges from approximately 0.5 cm to 1.0 cm wide. Mature foliage upper side: Center near RHS Green 137A. Margin near Yellow-White 158B. Margin width ranges from approximately 0.5 cm to 1.0 cm wide. Mature foliage under side: Center near RHS Green 137C. Margin near Yellow-White 158B. Margin width ranges from approximately 0.5 cm to 1.0 cm wide.
- *Venation*.—Type: Pinnate. Venation color upper side: Vein color indistinguishable from color of foliage blade. Venation color under side: Mid vein near Yellow 8C. Lateral veins indistinguishable from foliage blade.

Petiole: Not present, sessile.

FLOWER

Bloom period:
- *Natural season*.—January to March.

Inflorescence:
- *Arrangement*.—Single trumpet shaped flowers, composed of petaloid sepals clustered in terminal heads. Corolla not present.
- *Diameter*.—Approximately 5.0 cm to 7.0 cm.
- *Depth*.—Approximately 3.5 cm.
- *Quantity of flowers per inflorescence*.—Approximately 10 to 15 open flowers and buds.

Flower:
- *Facing direction*.—Out and up.
- *Diameter of entire flower*.—Approximately 1.7 cm.
- *Depth/length of flower*.—Approximately 1.6 cm.
- *Persistent or self-cleaning*.—Self-cleaning.
- *Fragrance*.—Moderately strong, sweet *Daphne* scent.

Bud:
- *Size*.—Approximately 7 mm long and 4 mm wide.
- *Shape*.—Conical.
- *Color*.—Near RHS Red-Purple 59C, apex near RHS Red-Purple 65A.

Petaloid sepals:
- *Quantity*.—4.
- *Length*.—Approximately 0.8 cm, excluding tube.
- *Width*.—Approximately 0.4 cm.
- *Apex*.—Acute.
- *Base*.—Fused.
- *Shape*.—Deltoid.
- *Margin*.—Entire.
- *Arrangement*.—Each petal opposite another, forming a cross.
- *Texture*.—Smooth upper and lower surfaces.

*Color*.—Upper surface at first opening: Near RHS Red-Purple 73D, margin flushed near RHS Purple 75C. Upper surface at maturity: Near RHS Red-Purple 69D. Upper surface at fading: Near RHS White N155B. Under surface at first opening: Near RHS Red-Purple 72D. Under surface at maturity: Near RHS Red-Purple 69B. Under surface at fading: Near RHS Red-Purple 69C.

Floral tube:

*Length*.—Approximately 0.6 cm.

*Diameter*.—Approximately 0.4 cm.

*Color*.—Outer surface at first opening: Near RHS Red-Purple N74D. Outer surface at maturity: Near RHS Purple 75C. Outer surface at fading: Near RHS Purple 75D. Inner surface at first opening: Near RHS Red-Purple 73D. Inner surface at maturity: Near RHS Red-Purple 69D. Inner surface at fading: Near RHS Red-Purple 69D.

Pedicle:

*Length*.—Average range 8 mm to 1.5 cm.

*Color*.—Near RHS Yellow-Green 144A.

REPRODUCTIVE ORGANS

Number of pistils per flower: 1.

*Pistil length*.—Approximately 0.6 cm.

*Stigma shape*.—Linear.

*Stigma color*.—Near RHS White N155B.

*Style color*.—Near RHS White N155B.

*Style length*.—Approximately 0.5 cm.

*Ovary color*.—Near RHS Yellow-Green 144C.

*Stamens quantity*.—Approximately 5 to 10. Stamens semi-fused to sepals.

*Stamen length*.—Approximately 0.2 cm.

*Stamen color*.—Near RHS White N155B.

*Anther shape*.—Linear.

OTHER CHARACTERISTICS

Disease and pest resistance: Not observed to be susceptible nor resistant to normal diseases and pests of *Daphne*.

Drought tolerance: Some drought tolerance. Plants will not wilt or suffer significant damage if regular supplemental waterings are missed.

Low temperature tolerance: Hardy to −20° C.

High temperature tolerance: High temperature tolerance is not exactly known. Tolerates at least 33° C.

Fruit/seed production: Not observed to date.

The invention claimed is:

1. A new and distinct cultivar of *Daphne* plant named 'MonMkie' as herein illustrated and described.

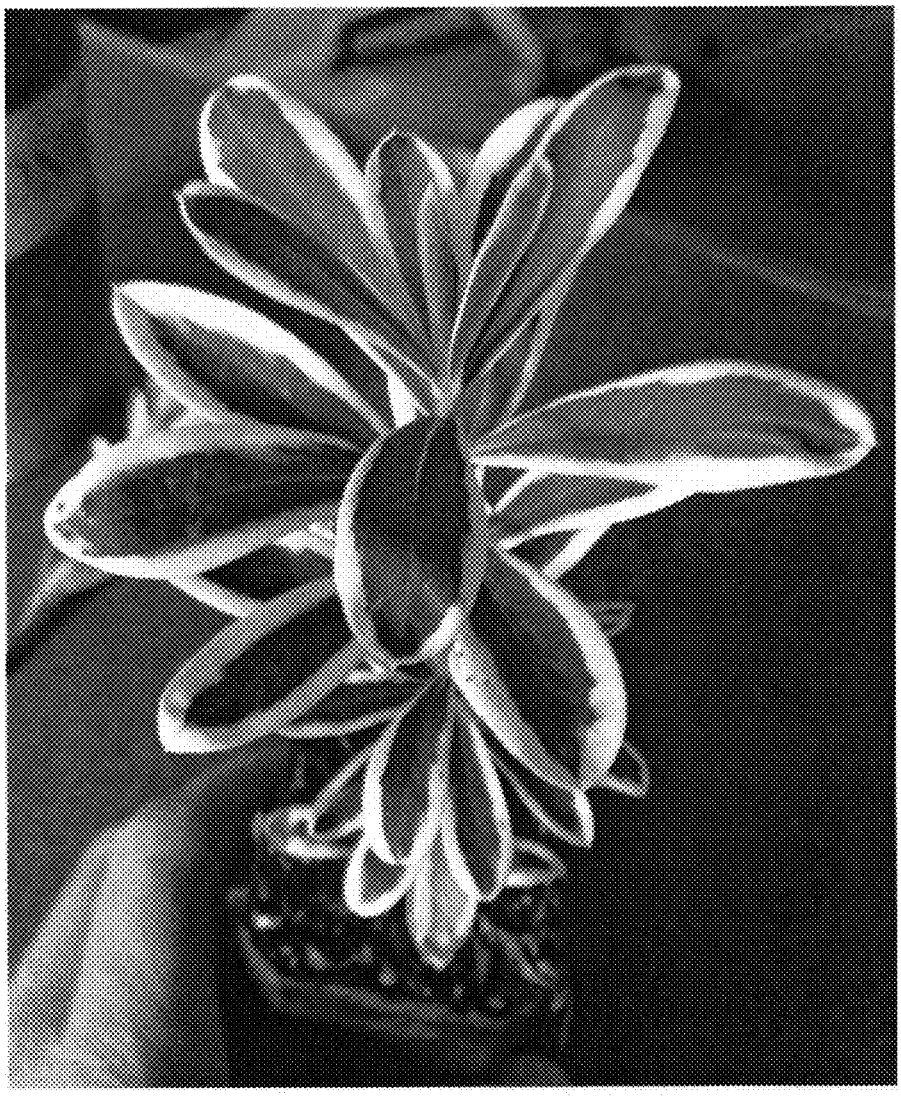

* * * * *